(12) United States Patent
Enriquez, III et al.

(10) Patent No.: US 7,770,365 B2
(45) Date of Patent: Aug. 10, 2010

(54) METHOD OF RETAINING SUTURE PACKAGES FOR THE DISPENSING OF SUTURES THERE FROM

(75) Inventors: John Marcos Enriquez, III, Henderson, NV (US); Kenneth Warren Volker, Las Vegas, NV (US)

(73) Assignee: Equinox Surgical Solutions, LLC, Reno, NV (US)

( * ) Notice: Subject to any disclaimer, the term of this patent is extended or adjusted under 35 U.S.C. 154(b) by 0 days.

(21) Appl. No.: 12/584,166

(22) Filed: Aug. 31, 2009

(65) Prior Publication Data

US 2009/0321468 A1 Dec. 31, 2009

Related U.S. Application Data

(62) Division of application No. 11/489,418, filed on May 10, 2006.

(51) Int. Cl.
B65B 43/00 (2006.01)
(52) U.S. Cl. ............................... 53/492; 53/390; 53/393
(58) Field of Classification Search ............... 53/381.1, 53/390, 393, 492; 206/63.3, 339, 380; 221/192, 221/276, 279
See application file for complete search history.

(56) References Cited

U.S. PATENT DOCUMENTS

| | | | |
|---|---|---|---|
| 557,553 A | 4/1896 | Chillberg | |
| 1,362,449 A | 12/1920 | Teall | |
| 2,910,066 A | 10/1959 | Kammer | |
| 3,185,482 A | 5/1965 | Russell | |
| 3,425,595 A | 2/1969 | Shapira | |
| 4,343,415 A | 8/1982 | Radek | |
| 4,372,465 A * | 2/1983 | Alcorn | 221/279 |
| 4,424,898 A * | 1/1984 | Thyen et al. | 206/63.3 |
| 4,501,379 A * | 2/1985 | Halone et al. | 221/221 |
| 5,048,720 A * | 9/1991 | Hoke | 221/276 |
| 5,228,565 A * | 7/1993 | Sinn | 206/63.3 |
| 5,230,424 A * | 7/1993 | Alpern et al. | 206/63.3 |
| 5,284,293 A | 2/1994 | Alpern et al. | |
| 5,350,060 A * | 9/1994 | Alpern et al. | 206/63.3 |
| 5,392,903 A * | 2/1995 | Sinn | 206/63.3 |
| 5,562,211 A * | 10/1996 | Simons et al. | 206/438 |
| 5,575,382 A * | 11/1996 | Sobel et al. | 206/63.3 |
| 5,806,278 A | 9/1998 | Shelledy | |
| 5,975,349 A | 11/1999 | Menes | |
| 6,000,589 A * | 12/1999 | Burdine | 221/279 |
| 2004/0129591 A1 | 7/2004 | Koseki | |
| 2006/0163270 A1 | 7/2006 | Ramey | |

* cited by examiner

*Primary Examiner*—Louis K Huynh
(74) *Attorney, Agent, or Firm*—Weide & Miller, Ltd

(57) ABSTRACT

A suture package retaining device having a housing with an interior space. Suture packages are located in an interior space of the housing and biased towards a top of the device. A top-most suture package is positioned at the top in alignment with an opening. The top-most suture package is held in position in the retaining device, permitting a user to access a suture of the package through the opening. When a user applies upward force to remove the suture, the suture package is maintained in a fixed position, allowing the user to disassociate the suture from the package. The device may include a slot through which suture packages may be inserted into or removed from the interior space.

9 Claims, 2 Drawing Sheets

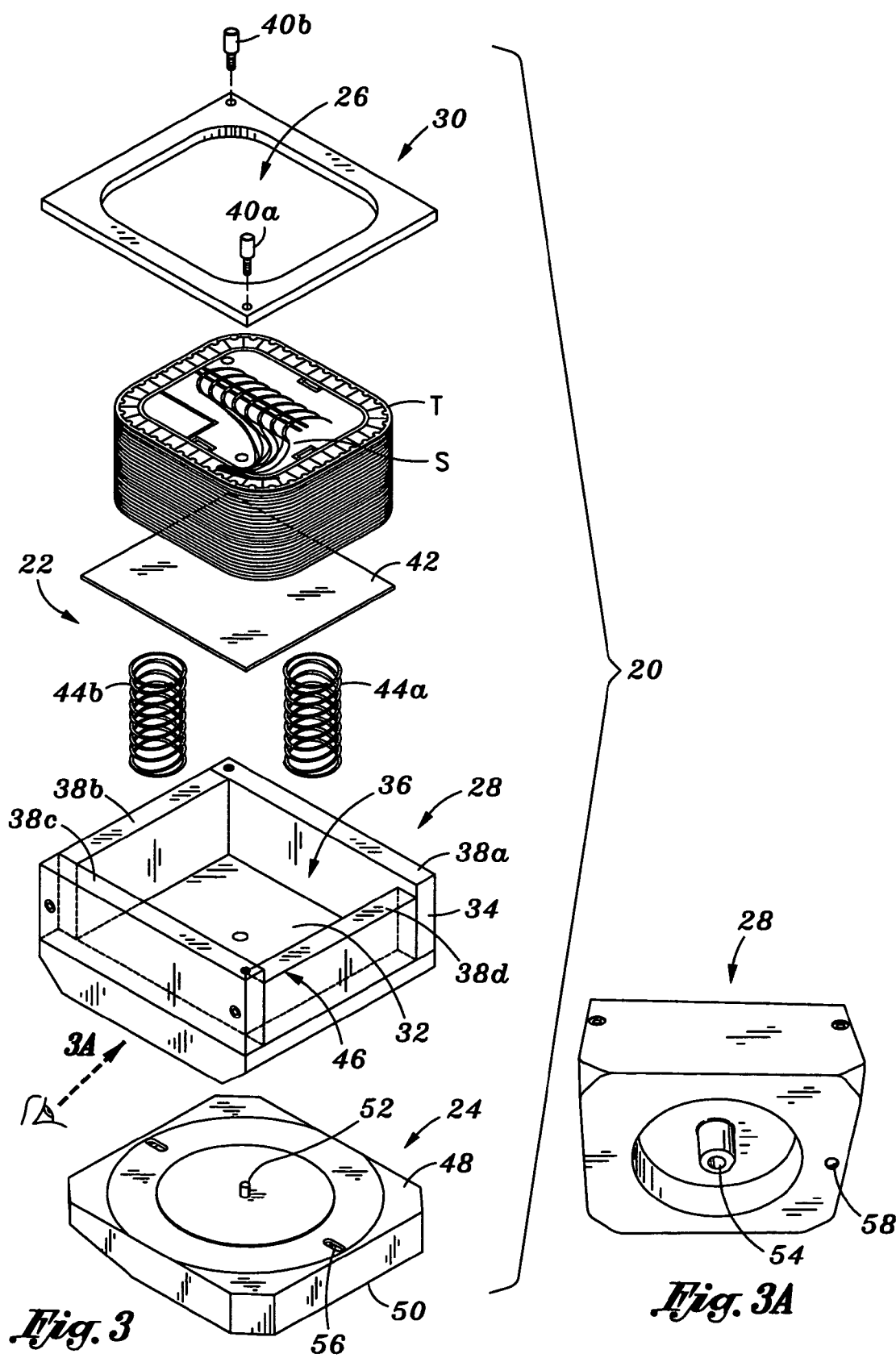

METHOD OF RETAINING SUTURE PACKAGES FOR THE DISPENSING OF SUTURES THERE FROM

RELATED APPLICATION DATA

This application is a divisional of U.S. application Ser. No. 11/489,418, filed May 10, 2006.

FIELD OF THE INVENTION

The present invention relates to a method and apparatus for dispensing sutures.

BACKGROUND OF THE INVENTION

Sutures are commonly used in the medical field, such as in the surgical environment. Often, sutures are supplied with an integrated needle, otherwise known as atraumatic needles with sutures. These sutures are generally pre-packaged for shipping and then use. The packaging may be a relatively light-weight molded plastic tray which is sealed in a package. This packaging has the advantage that the tray and sutures can be maintained in a sterile environment before use, and is cheap and convenient to ship and store. An example of a suture tray with associated sutures is illustrated in FIGS. 1-3 herein as associated with a suture dispenser of the present invention.

Unfortunately, a number of problems arise when using the sutures. In a surgical environment, the suture package is opened and the tray of sutures is removed. The tray of sutures may then be placed on a table. The individual sutures must then be removed from the tray as needed.

Very frequently, the medical personnel which requires a suture or is to provide the suture has only a single hand free. For example, a surgical technician who is assisting a surgeon may provide a suture to the surgeon. The surgical technician, however, is often holding a retractor or other object with one hand. This then requires that the technician acquire a suture with their other hand. This is very difficult considering how the sutures are packaged. The medical personnel usually grasps one of the needles associated with the suture and then attempts to dislodge the needle and suture from the package. Most commonly, each needle is press-fit to a portion of the tray, and the corresponding sutures are routed around a peripheral portion of the package. As such, the medical personnel must attempt to pop the needle loose from the package and then pull the suture from the package, using one hand.

Because the package is relatively small and is lightweight, an upward force on the needle or suture to dislodge it from the package generally causes the package to similarly move, thwarting the person's attempt to obtain the suture. In extreme cases, quick movement of the needle and suture may cause the tray to become airborne and it may swing or move about, hitting other objects. If the suture comes loose from the package when this occurs, the tray may actually travel some distance. It might then land on the floor, hit a patient or the like, all of which are undesirable.

SUMMARY OF THE INVENTION

The present invention comprises embodiments of suture dispensers and methods of dispensing sutures.

In one embodiment, a suture dispenser comprises a housing having a bottom, at least one wall extending upwardly from the bottom and a top located generally opposite the bottom. The housing defines a generally enclosed interior space for housing at least one suture package having an associate suture, at least one window through which sutures may be accessed, and a suture package support located in the interior space which is biased upwardly towards the top of the housing so that a top-most suture package is located adjacent the opening, whereby a user may remove a suture associated with the top-most suture package through the opening.

When configured to hold generally rectangular-shaped suture packages or trays, the at least one wall of the housing may be generally rectangular in shape. For example, the wall may have four sides and thus define a generally rectangular-shaped interior space.

In one embodiment, the top is defined by or comprises a cover. The cover may be moveable with respect to the housing, thereby providing access to the interior space. The cover may be selectively attached to the housing with one or more threaded fasteners.

Preferably, the opening in the top or cover is smaller than the size of the suture container. In this manner, at least a portion of the top or cover engages a top-most suture container, maintaining the suture container(s) within the interior space.

In one embodiment the suture package support comprises a plate. The plate is biased upwardly, such as by one or more springs positioned between it and the bottom of the housing.

The housing may define one or more slots or other additional openings leading to the interior space. In one embodiment, a portion of the wall does not extend to the top or cover, thereby creating a slot near the top of the housing. The suture packages may be loaded into the interior space through the slot, or removed from the housing through the slot.

The suture dispenser may include a stand. The stand has a bottom surface for engagement with a support surface. The housing is connected to the stand. In one embodiment, the housing is rotatably mounted to the stand.

In use, one or more suture packages may be loaded into the suture dispenser. The suture packages might comprise, for example, trays having one or more associated sutures.

The sutures may be loaded into the interior space by inserting them through the slot(s) in the housing (if provided) or by moving or removing the cover to provide access to the interior space (if so configured). When trays are loaded, the suture package support may be compressed towards the bottom of the housing. Thereafter, the suture package support presses the suture package(s) upwardly towards the top of the housing. In his position, at least the top-most suture package is preferably positioned adjacent the opening in the housing.

A user may grasp a suture or needle associated with a suture of the package by reaching through the opening. The user may remove the suture and/or associated needle by applying a disconnecting force. Notably, the suture package is maintained in position within the housing. In particular, the housing engages the suture package, preventing its movement, thereby permitting the disconnecting force to cause the suture to disengage from the package.

Once the suture or sutures associated with a package have been removed or the package is otherwise used, the package may be removed from the housing. The suture package may be slid out through the slot or via moving or removing the cover. When there are additional suture packages located in the housing, the next package is pressed upwardly into position for use.

In accordance with the invention, a user can quickly and easily access sutures. The sutures can be removed from their packaging with one hand. The sutures are also conveniently and safely stored.

Further objects, features, and advantages of the present invention over the prior art will become apparent from the detailed description of the drawings which follows, when considered with the attached figures.

DESCRIPTION OF THE DRAWINGS

FIG. 3 is an exploded view of the suture dispenser illustrated in FIGS. 1 and 2; and FIG. 3A is a bottom view of a base portion of a housing of the suture dispenser illustrated in FIGS. 1-3.

DETAILED DESCRIPTION OF THE INVENTION

The invention comprises methods and apparatus for dispensing sutures. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In general, the invention is a suture dispenser and method of dispensing sutures. The invention has particular utility to sutures which are associated with packaging, such as trays. In one embodiment, the invention is a dispenser which comprises a housing for containing one or more trays or other packages of sutures, the housing configured to secure the tray or package in a manner which permits the one or more sutures to easily be removed or disconnected from the tray.

Figure 1:
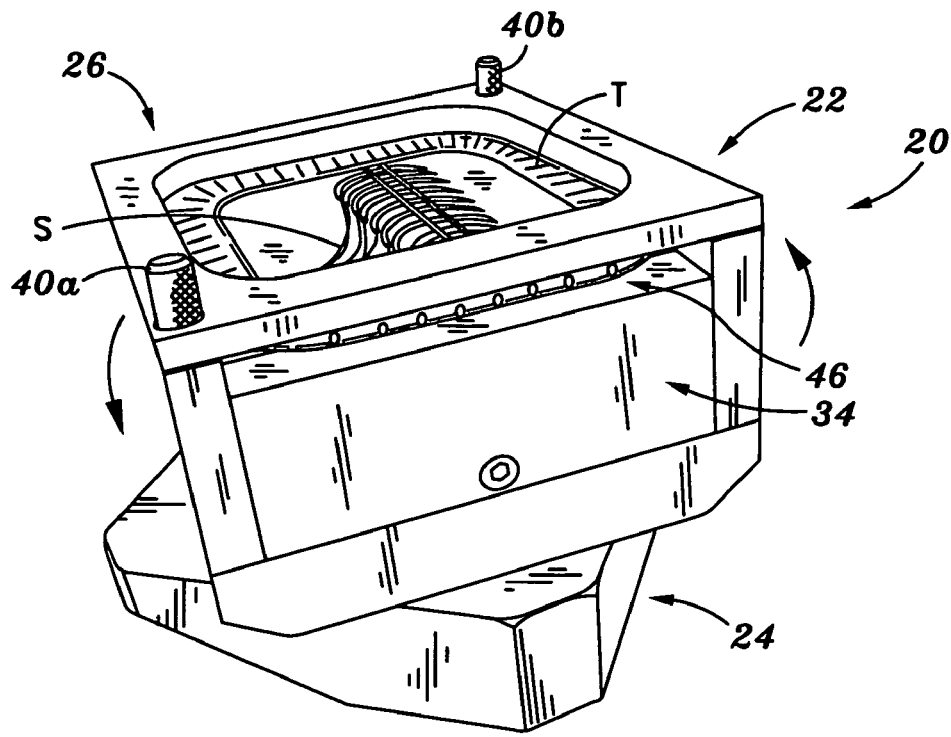
FIG. 1 is a perspective view of a suture dispenser in accordance with one embodiment of the invention.

One embodiment of a suture dispenser 20 will be described in greater detail with reference to FIGS. 1-3A. As illustrated in FIG. 1, the suture dispenser 20 comprises a housing 22 and a stand 24. In general, the housing 22 defines an area for the storage of one or more sutures, such as one or more packages having associated sutures. The housing 22 has a bottom and at least one wall extending upwardly to a top. The housing 22 preferably defines at least one opening or window 26 which provides access to the one or more stored sutures. In one embodiment, the housing 22 is mounted to the stand 24. In a preferred embodiment, the housing 22 is mounted for movement relative to the stand 24.

Referring to FIG. 3, in one embodiment, the housing 22 comprises a base 28 and a cover or lid 30. The base 28 and lid 30 cooperate to define an interior space or area 36 which is at least partially enclosed.

In one embodiment, the base 28 has a bottom 32 and an upstanding wall 34 which at least partially define the interior area 36. In one embodiment, the suture dispenser 20 is particularly configured to house generally rectangular trays or packages of sutures. In such an embodiment, the base 28 may have a similar configuration. As illustrated, the bottom 32 may be generally rectangular in peripheral shape. Similarly, the upstanding wall 34 may have four sides 38*a, b, c, d*. First and second opposing sides 38*a,c* extend generally parallel to one another. Third and fourth opposing sides 38*b,d* extend parallel to one another and generally perpendicular to the first and second sides 38*a,c*. In such a configuration, the interior area 36 may be generally rectangular in peripheral shape.

The wall 34 may be formed from one or more elements. Those one or more elements may be connected to the bottom 32. In another embodiment, the wall 34, or at least one or more portions thereof, may be formed integrally with the bottom 32. For example, the base 28 may essentially comprise a body having a depression formed therein.

The wall 34 has a top end generally opposite the base 28. In a preferred embodiment, the top of the housing 34 is generally defined by a top or cover 30. The cover 30 is located at the top of the wall 34. In one embodiment, the cover 30 is movable between at least a first position and a second position relative to the base 28. As illustrated, fastening means are provided for selectively connecting the cover 30 to, and disconnecting the cover 30 from, the base 28. The fastening means comprise first and second threaded fasteners 40*a,b* which may be passed through apertures in the cover 30 into engagement with the base 28 and, more particularly, the wall 34. The cover 30 could be mounted in other manners, however, to permit movement or removal thereof. For example, the cover 30 may be connected to the base 28 by a hinge, or might be connected with clips or pins.

In a preferred embodiment, the window or opening 26 of the suture dispenser 20 is located at the top of the housing 22. Where the top of the housing 22 is defined by the cover 30, the opening is preferably defined by the cover 30. As illustrated, the cover 30 comprises a relatively thin plate which defines the opening 26 therein. For reasons described in detail below, the size of the opening 26 is preferably less than the size of a suture package to be retained in the housing 22, and thus also smaller in peripheral dimension than the peripheral dimension of the interior area 36 of the base 28.

In one embodiment, as illustrated, the opening 26 is defined within the cover 30. In other embodiments, the opening might only be partially defined or surrounded by the cover 30. There might also be more than one opening.

As described in detail below, in a preferred embodiment, one or more sutures located in the housing 22 are preferably biased upwardly towards the opening 26 for access by a user of the dispenser 20. The suture dispenser 20 includes means for biasing sutures upwardly within the housing 22. In one embodiment, this means comprises a suture support 42 and means for biasing the support.

Figure 2:
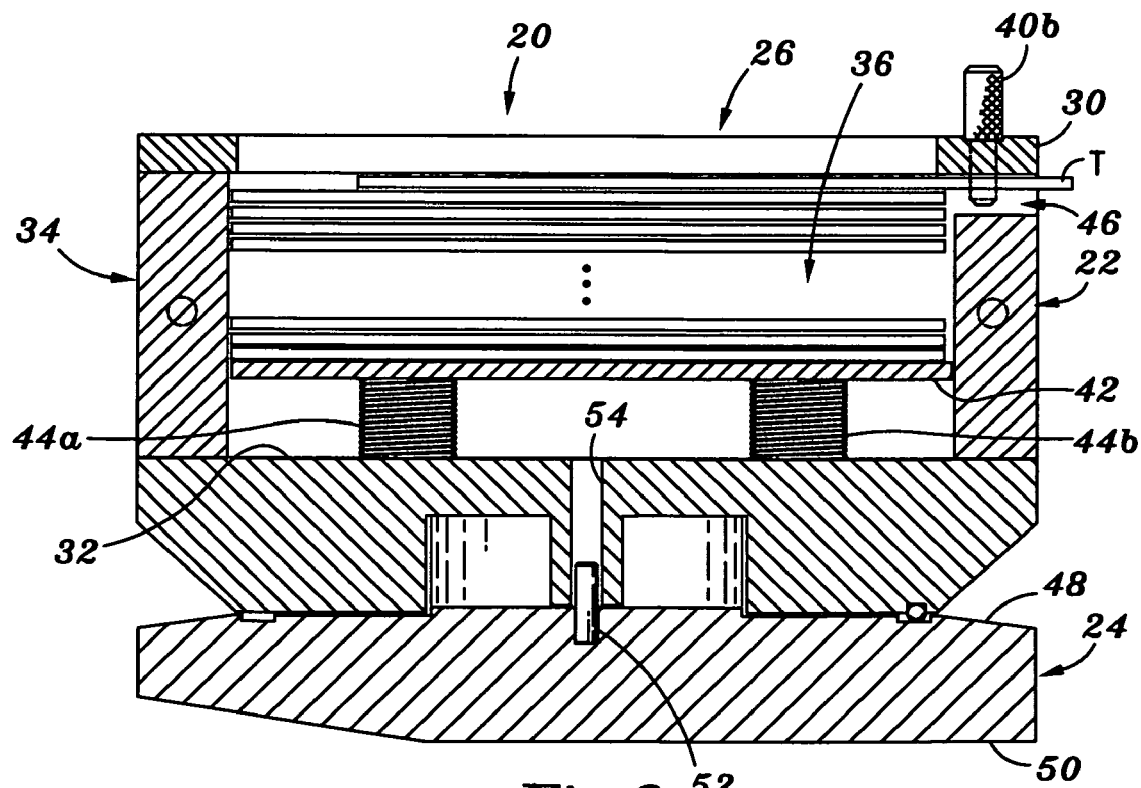
FIG. 2 is a cross-sectional side view of the suture dispenser illustrated in FIG. 1.

As illustrated in FIGS. 2 and 3, the means for biasing the support comprises a pair of springs 44*a,b*. The springs 44*a,b* are located between the bottom 32 of the base 28 and a bottom of the plate 42, whereby the plate 42 is biased upwardly towards the cover 30. In one embodiment, the springs 44*a,b* are coil springs. The length of the springs 44*a,b* are chosen so that when they are fully extended, the plate 42 is located proximate to the cover 30. Of course, other means for biasing might be utilized, such as one or more flexible members, such as a diaphragm.

As described in more detail below, in one embodiment, sutures may be loaded for use and unused sutures or remaining packaging may be removed from the housing 22, preferably without changing the position of the cover 30 from its connected position. In one embodiment, the housing 22 defines a slot 46 or other opening (in addition to the main opening 26).

In the embodiment illustrated, the slot 46 is defined by the base 28 and cover 30. At least a portion of the wall 34 is set back from the cover 30 when the cover 30 is connected thereto, thereby defining the slot 46. In one embodiment, one of the sides 38*d* of the wall 34 is shorter than the other sides 38*a,b,c* by a distance which is preferably at least as great as the thickness of a suture or suture package.

As indicated, in one embodiment, the suture dispenser 20 includes a stand 24. In a preferred embodiment, the housing 22 can be moved relative to the stand 24. The housing 22 may also be removable from the stand 24.

Still referring to FIGS. 2 and 3, in one embodiment the stand 24 has a top 48 and a bottom 50. When connected, the bottom 32 of the base 28 of the housing 22 is located adjacent the top 48 of the stand 24.

In one embodiment, the housing 22 is configured to move relative to the stand 24. As illustrated, a pin or post 52 extends upwardly from the top 48 of the stand 24. Referring to FIG. 3A, the base 28 of the housing 22 defines an aperture 54 for accepting the pin 52. In this manner, the housing 22 may be rotated about the pin 52, relative to the stand 24. As illustrated, the bottom 32 of the base 28 of the housing 22 and the top 48 of the stand 50 are otherwise relatively smooth to not interfere with this rotation.

The housing 22 may be connected to the stand 24 permanently. In another embodiment, the housing 22 may be removable from the stand 24 (such as illustrated in FIG. 3).

In one embodiment, the bottom 50 of the stand 24 is not flat, but defined as at least two surfaces which lie in different planes. In this manner, the stand 24 may be oriented so that the top 48 thereof is generally horizontal (as illustrated in FIG. 2), or so that the top 48 is positioned at an angle offset from horizontal (as illustrated in FIG. 1). This permits the orientation of the housing 22, and thus the position of the opening 26, to be changed.

In one embodiment, means may be provided for selectively retaining the housing 22 in a fixed position relative to the stand 24. Referring to FIGS. 2, 3 and 3A, the stand 24 may include one or more depressions 56 for accepting a ball 58 or other protrusion from the bottom 28 of the housing 22. Location of the ball 58 in a mating depression generally maintains the stand 24 in position. Sufficient force will dislodge the ball 58 from the depression, allowing the housing 22 to easily rotate about the stand 24. In one embodiment, the depressions are in positions corresponding to commonly used positions for the housing (such as a first position and another position 90 degrees with respect thereto).

A method of using the suture dispenser 20 will now be described. Sutures may be loaded into the housing 22. In one embodiment, sutures S which are associated with a suture package, such as a tray T, are loaded into the housing 22. The one or more suture trays T may be loaded into the interior 36 of the base 28 of the housing 22 by either removing the cover 30 or sliding them through the slot 46 in the housing 22.

Referring to FIG. 2, the housing 22 preferably has sufficient depth that a plurality of layers of trays T may be located therein. As illustrated, as trays T are loaded, the plate 42 is pressed downwardly, compressing the springs 44a,b. The trays T are biased upwardly, however, with the top-most tray T abutting the cover 30.

As indicated above, the opening 26 in the cover 30 is preferably smaller than the tray T. In this manner, the central section of the tray T, and thus the sutures S mounted thereon, may be accessed through the opening 26. On the other hand, the portion of the cover 30 which surrounds the opening 26 engages the outer portion of the top-most tray T, thereby retaining the tray(s) T in the housing 22.

As described above, in one embodiment the orientation of the housing 22 relative to the stand 24 may be changed. The housing 22 may be rotated relative to the stand 24, as best illustrated in FIG. 1. In this manner, the user may turn the housing 22 to the position which best enables them to reach the sutures S. In addition, the position of the stand 24 may be changed relative to a support surface. The stand 24 may be oriented so that the top 48 thereof is horizontal, as is the housing 22. Alternatively, the stand 24 may be "tipped" so that the housing 22 is no longer horizontal but instead is oriented at an angle.

In use, the user may grasp a needle and remove it and its associated suture from the tray T. The needle is readily accessible through the opening 26 in the housing 22. Most importantly, when the user grasps the needle and attempts to pull it and its associated suture from the tray T (by applying a "dislodging" or "disconnecting" force), movement of the tray T is limited. In particular, the tray T is restrained by the housing 22. As such, when the user pulls on the needle and suture, the needle and suture readily disconnect from the associated tray. It is noted that the size and weight of the housing 22 (and associated stand 24) are such that this action also does not result in movement of the dispenser 20. In particular, the force needed to disconnect the needle and suture from the tray is much less than that necessary to move or pick up the dispenser 20.

When all of the sutures S associated with a particular tray T have been utilized, or when it is otherwise desirable to remove one of the trays T, the tray T may be slid out the slot 46 (or removed after removing or moving the cover 30, though this is the less desirable option). When the top tray T is removed, the plate 42 presses the next tray upwardly into position.

The suture dispenser of the invention may have a wide variety of configurations. In one embodiment, the elements comprising the suture dispenser are constructed of a sterilizable material. Preferably, the dispenser is constructed so that it has significant weight—when considering its size and/or the materials used. In this manner, the dispenser will not readily move when sufficient force is applied to a needle and associated suture to remove them from a tray. For example, the various elements of the dispenser may be constructed of stainless steel.

The dispenser need not include a stand, though one is preferred. In one embodiment, for example, the dispenser may simply comprise a housing and the housing may rest directly upon a support surface. If a stand is utilized, the housing may engage the stand in other fashions. For example, the housing might be configured to slide into engagement with the stand. The housing might include a pin which extends outwardly into engagement with the stand. The housing and stand might include a mating slot and track. For example, the stand might define a circular groove and the housing might define a circular tab which can be placed into alignment with the groove, the tab being rotatable within the groove.

As indicated, in one embodiment the sole access to the interior of the housing might be by moving or removing the cover (i.e. the housing might not include a slot). Likewise, the cover might not be movable or removable and instead all access might be through the slot.

The location of the slot and/or its size might vary. Preferably the slot is located near the top of the housing so that a top, used tray may be conveniently removed. The housing might, for example, include two slots: one at near the bottom for loading new trays/sutures and one near the top for removing used trays. The housing might also define one or more slots in other locations (such as slots at opposing sides of the housing.

As indicated above, in one embodiment, the suture packages or trays are biased upwardly into engagement with the top or cover of the housing. The housing could also include a stop, such as an internal shelf or the like, which serves to limit the upward travel. In this manner, for example, the cover might be removable without the trays or packages automatically springing out of the housing.

In one embodiment, various of the components of the dispenser may comprise separate elements or instead be connected. For example, as detailed above, the housing might comprise a singular element (such as molded or machined), but might also comprise an assembly of elements (such as individual wall sections connected to one another and the base or bottom).

It will be appreciated that the dispenser might include more than one housing or a housing configured to store or house multiple "stacks" of suture packages.

In one embodiment, the suture dispenser, or at least a portion thereof, may be configured to be disposable. In this manner, patient safety is enhanced because a new sterile suture dispenser can be used for each surgical procedure. In one embodiment, the suture dispenser may be constructed from plastic (such as in a molding process) so as to be quickly and inexpensively manufactured. For example, the base and cover of the housing may be molded. A molded tray support member may be connected to a pair of springs and then be located in the base. The cover may then be secured to the base.

In such an embodiment, the housing might be connected to a support surface via adhesive (for example, adhesive tape may be located on the bottom of the housing) or other means of connection so as to secure it in position (since the dispenser may otherwise then be of insufficient mass to prevent its movement when a suture is retrieved). In another embodiment, a disposable housing might be connectable to a heavy stand (such as one constructed of stainless steel). For example, the housing might be configured to slip over a pin extending from the stand. The stand might include a spring loaded ball or similar element for mating with a recess in the housing to secure the housing to the stand under normal use conditions (but permitting the housing to be separated for disposal). Of course, the housing might be connected to the stand in other manners (such as by sliding engagement, as detailed above).

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A method of dispensing sutures comprising:
   locating at least one suture package having at least one associated suture in an interior of a housing of a suture dispenser;
   biasing said at least one suture package upwardly towards a top of said housing of said suture dispenser so that a top-most package is positioned adjacent an opening in a top of said housing;
   retaining said top-most suture package in a fixed position by engagement of said top-most suture package with said housing of said suture dispenser;
   grasping a needle of a suture associated with said top-most suture package through said opening of said housing of said suture dispenser; and
   applying a removing force to said needle and associated suture to disassociate said needle and suture from said top-most suture package while said suture package is retained in said housing.

2. The method in accordance with claim 1 wherein said top of said housing is defined by a cover, said cover defining said opening.

3. The method in accordance with claim 2 wherein said locating step comprises removing a cover of said housing and inserting said at least one suture package within said housing.

4. The method in accordance with claim 2 wherein said suture package has a peripheral edge and a central portion and said step of retaining said top-most suture package comprises positioning said peripheral edge of said top-most suture package against said housing with said central portion thereof accessible through said opening.

5. The method in accordance with claim 1 including the step of removing said top-most suture package from said housing after use thereof by sliding said top-most suture package out of a slot in a side of said housing.

6. A method of retaining a suture package and dispensing sutures there from comprising the steps of:
   providing a suture package retaining device comprising a housing having a cover having an opening therein said device having an interior space within said housing, a suture package support located in said interior space, said suture package support biased upwardly towards said cover;
   positioning at least one suture package having at least one suture connected thereto in said interior space of said suture package retaining device;
   biasing said at least one suture package upwardly towards said cover with said suture package so that a top-most package is positioned adjacent said opening in said cover;
   retaining said top-most suture package in a fixed position by engagement of said top-most suture package with said housing of said suture dispenser;
   grasping a needle of a suture associated with said top-most suture package through said opening of said housing of said suture dispenser; and
   removing said suture from said at least one suture package while said top-most suture package remains in a fixed position in said housing.

7. The method in accordance with claim 6 wherein said step of retaining comprises biasing said top-most suture package upwardly against a bottom of said cover.

8. The method in accordance with claim 7 comprising the step of automatically moving a next suture package upwardly against said cover after said top-most suture package is removed.

9. The method in accordance with claim 6 further comprising the step of removing said top-most suture package from said suture package retaining device after at least one suture has been removed from said top-most suture package, said step comprising sliding said top-most suture package from said device through a slot located below said cover.

* * * * *